US012691162B2

(12) United States Patent
Vallabhbhai et al.

(10) Patent No.: US 12,691,162 B2
(45) Date of Patent: Jul. 28, 2026

(54) MULTI-DOSE PEN OF TIRZEPATIDE

(71) Applicant: ORBICULAR PHARMACEUTICAL TECHNOLOGIES PRIVATE LIMITED, Hyderabad (IN)

(72) Inventors: Patel Bhaveshkumar Vallabhbhai, Hyderabad (IN); Raghu Kannekanti, Hyderabad (IN)

(73) Assignee: ORBICULAR PHARMACEUTICAL TECHNOLOGIES PRIVATE LIIMTED, Hyderabad (IN)

( * ) Notice: Subject to any disclaimer, the term of this patent is extended or adjusted under 35 U.S.C. 154(b) by 0 days.

(21) Appl. No.: 19/062,335

(22) Filed: Feb. 25, 2025

(65) Prior Publication Data

US 2026/0014233 A1 Jan. 15, 2026

(30) Foreign Application Priority Data

Jul. 11, 2024 (IN) ............................ 202441053093

(51) Int. Cl.
*A61K 38/26* (2006.01)
*A61K 9/00* (2006.01)
*A61K 9/08* (2006.01)
*A61K 47/10* (2017.01)

(52) U.S. Cl.
CPC ............ *A61K 38/26* (2013.01); *A61K 9/0019* (2013.01); *A61K 9/08* (2013.01); *A61K 47/10* (2013.01)

(58) Field of Classification Search
CPC ........ A61K 38/26; A61K 9/0019; A61K 9/08; A61K 47/10
See application file for complete search history.

(56) References Cited

U.S. PATENT DOCUMENTS

| | | | |
|---|---|---|---|
| 11,357,820 B2 | 6/2022 | Corvari et al. | |
| 2017/0008928 A1* | 1/2017 | Kruse .................... | A61K 47/10 |
| 2021/0338781 A1 | 11/2021 | Benson et al. | |

FOREIGN PATENT DOCUMENTS

| | | |
|---|---|---|
| CN | 215083461 U | 12/2021 |
| WO | 2011/109205 A2 | 9/2011 |
| WO | 2023/238017 | 12/2023 |
| WO | 2024/006662 | 1/2024 |
| WO | 2024/086601 A2 | 4/2024 |

OTHER PUBLICATIONS

Wong et al., Am. J. Therapeuitcs 30, e26-35 (2023).*
Forzano, et al., "Tirzepatide: a Systematic Update," Int J Mol Sci., 23(23):14631 (2022).
International Search Report in PCT/IB2025/051994 mailed Jun. 25, 2025.

* cited by examiner

*Primary Examiner* — Gyan Chandra
(74) *Attorney, Agent, or Firm* — MEDLER FERRO WOODHOUSE & MILLS PLLC

(57) ABSTRACT

The present invention relates to a liquid pharmaceutical composition of tirzepatide or pharmaceutically acceptable salt or derivative(s) thereof delivered with a multi-dose pen. Further the present invention relates to a reusable or disposable pen comprises one or more cartridge(s) suitable for delivering multiple doses of tirzepatide for the treatment of tirzepatide sensitive diseases. The present invention also relates to a novel liquid pharmaceutical composition comprising tirzepatide in a concentration of 67 mg/mL to 200 mg/mL, wherein such composition is substantially free from sodium chloride, and wherein such composition exhibits long-term stability suitable for storage.

10 Claims, No Drawings

MULTI-DOSE PEN OF TIRZEPATIDE

FIELD OF THE INVENTION

The present invention relates to a liquid pharmaceutical composition of tirzepatide or pharmaceutically acceptable salt or derivative(s) thereof delivered with a multi-dose pen. Further the present invention relates to a reusable or disposable pen comprises one or more cartridge(s) suitable for delivering multiple doses of tirzepatide for the treatment of tirzepatide sensitive diseases. The present invention also relates to a novel liquid pharmaceutical composition comprising tirzepatide in a concentration of 67 mg/mL to 200 mg/mL, wherein composition is substantially free from sodium chloride, and wherein such composition exhibits long-term stability suitable for storage.

BACKGROUND OF THE INVENTION

The rapid development of modernization, urbanization, and accelerated socio-economic growth favored an improved living standard but a more stressful and sedentary lifestyle and unhealthy dieting habits in most parts of the world. Especially in the last two decades, obesity has become a global pandemic threatening people's life by affecting almost every organ system and is now a severe public health problem as one of the most common non-communicable diseases (NCDs). With no exception, all countries are now being affected by obesity, and this impact is predicted to be even more prominent during the current decade, resulting in more lost years of a healthy life, disability, and death. Hence, it is urgent to make effective and decisive actions to hinder the rise in the prevalence of obesity to prevent and treat obesity and other obesity-related comorbidities, among which T2DM is a health issue growing at an alarming speed in all regions as another global health emergency of the 21st-century. The booming increase in the prevalence of obesity in all age groups is one of the main culprits of the exponential growth of the population of T2DM. (Ruze at al; *Endocrinol., Sec. Diabetes: Molecular Mechanisms* Volume 14—2023)

Type 2 diabetes mellitus (T2DM) is an expanding global health problem, closely linked to the epidemic of obesity. Individuals with T2DM are at high risk for both microvascular complications (including retinopathy, nephropathy and neuropathy) and macrovascular complications (such as cardiovascular comorbidities), owing to hyperglycemia and individual components of the insulin resistance (metabolic) syndrome. Environmental factors (for example, obesity, an unhealthy diet and physical inactivity) and genetic factors contribute to the multiple pathophysiological disturbances that are responsible for impaired glucose homeostasis in T2DM. Insulin resistance and impaired insulin secretion remain the core defects in T2DM, but at least six other pathophysiological abnormalities contribute to the dysregulation of glucose metabolism. The multiple pathogenetic disturbances present in T2DM dictate that multiple antidiabetic agents, used in combination, will be required to maintain normoglycaemia. The treatment must not only be effective and safe but also improve the quality of life. Several novel medications are in development, but the greatest need is for agents that enhance insulin sensitivity, halt the progressive pancreatic β-cell failure that is characteristic of T2DM and prevent or reverse the microvascular complications. (DeFronzo, R., Ferrannini, E., Groop, L. et al. *Type* 2 *diabetes mellitus. Nat Rev Dis Primers* 1, 15019 (2015))

A new molecule with a combined agonist action on both GPI and GLP1 receptors ("twincretin") has been developed to take advantage of this synergistic effect: Tirzepatide (LY3298176) is the first "twincretin", a synthetic peptide composed of 39 amino acids based on the GIP native sequence, combining the dual agonism of GIP and GLP-1 receptors controlling glycemic blood level and reducing body weight. Tirzepatide has an affinity for the GIP receptor equal to that of native GIP and an affinity for the GLP-1 receptor ~5-fold weaker than that of native GLP-1. Tirzepatide can also improve parameters related to cardiovascular risk, including blood pressure (BP), waist circumference, LDL, and circulating triglycerides. Both its effectiveness and safety have been demonstrated in several clinical trials. (Forzano et al *Int J Mol Sci.* 2022 Nov. 23; 23 (23):14631)

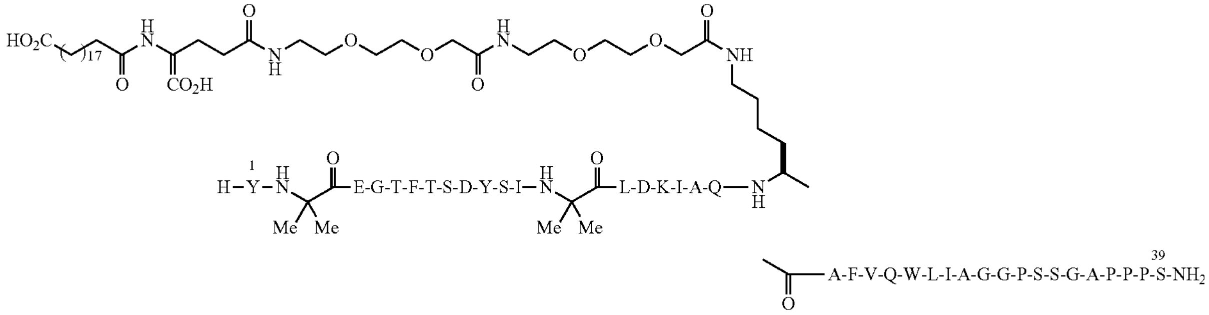

Tirzepatide Structural Formula

Currently Tirzepatide (MOUNJARO) is commercially available as once weekly subcutaneous injection for adjunct to diet and exercise to improve glycemic control in adults with type 2 diabetes mellitus with 06 strengths [2.5 mg/0.5 ml (2.5 mg/0.5 ml), 5 mg/0.5 ml (5 mg/0.5 ml), 7.5 mg/0.5 ml (7.5 mg/0.5 ml), 10 mg/0.5 ml (10 mg/0.5 ml), 12.5 mg/0.5 ml (12.5 mg/0.5 ml) and 15 mg/0.5 ml (15 mg/0.5 ml)] and Tirzepatide (ZEPBOUND) is commercially available as once weekly subcutaneous injection for adjunct to a reduced-calorie diet and increased physical activity for chronic weight management in adults with an initial body mass index (BMI) of: ·30 kg/m2 or greater (obesity) or ·27 kg/m2 or greater (overweight) in the presence of at least one weight-related comorbid condition (e.g., hypertension, dyslipidemia, type 2 diabetes mellitus, obstructive sleep apnea, or cardiovascular disease) with 06 strengths same as MOUNJARO.

There are many approved therapies for treatment of diabetes such as semaglutide (OZEMPIC) [once weekly], exenatide (BYDUREON BCISE) [once weekly], exenatide synthetic (BYDUREON) [once weekly], BYDUREON PEN [once weekly], BYETTA [twice daily], and liraglutide recombinant (VICTOZA) [once daily].

Further, there are many approved therapies for treatment of chronic weight management such as liraglutide (SAXENDA) [once daily], semaglutide (Wegovy) [once weekly], and setmelanotide (IMCIVREE) [once daily].

Currently USFDA approved peptides, contain sodium chloride in their approved composition: Semaglutide (WEGOVY)—Sodium Chloride (8.25 mg); Tirzepatide (MOUNJARO)—Sodium Chloride (4.1 mg); Tirzepatide (ZEPBOUND)—Sodium Chloride (4.1 mg) and Exenatide (BYDUREON)—Sodium Chloride (4.1 mg).

U.S. Pat. No. 9,474,780 B2 patent discloses GIP and GLP-1 co-agonist compounds includes tirzepatide drug substance. Further discloses GIP and GLP-1 co-agonist compounds useful for treating type 2 diabetes mellitus (T2D).

U.S. Pat. No. 11,357,820 B2 patent discloses pharmaceutical GIP/GLP1 co-agonist peptide composition. Further discloses composition comprises tirzepatide, sodium chloride, and dibasic sodium phosphate and an alternative formulation comprises tirzepatide, propylene glycol, and dibasic sodium phosphate. It also discloses tirzepatide composition further comprising one or more preservatives, and the preservative is selected from the group comprising of metacresol and phenol. The disclosed composition suitable for administration using an automatic injection apparatus, wherein the dose is administered once weekly. It also discloses embodiments reciting tirzepatide concentrations from about 5 mg/mL to about 30 mg/mL. This patent thus discloses a concentration of 30 mg/mL at the highest point of the disclosed range.

PCT Application WO2011109205A2 discloses an automatic injection apparatus including a delay mechanism for properly delivering medication prior to the needled syringe of the apparatus being retracted.

United States 2021/0338781A1 patent publication particularly the discloses at paragraph 0584 "The doses of the present invention are likely to have specific concentrations of 5 mg/mL, 10 mg/mL, 15 mg/mL, 20 mg/mL, 25 mg/mL and 30 mg/mL . . . . Such pre-filled syringe may be useful for administering one half milliliter of such composition per patient per dose." This publication discloses a concentration of 30 mg/mL at the highest point of the disclosed range.

US FDA approved Tirzepatide (MOUNJARO), is available as clear, colorless to slightly yellow solution in prefilled single-dose pens or single-dose vials and Tirzepatide (ZEPBOUND), is available as clear, colorless to slightly yellow solution available in pre-filled single-dose pens.

EU EMA approved Tirzepatide (MOUNJARO KwikPen), is available as clear, colorless to slightly yellow solution in pre-filled pen, multiple-dose KwikPen.

Approved injectable (ZEPBOUND, MOUNJARO & MOUNJARO KwikPen) tirzepatide compositions has one of the major drawbacks is that the injectable dosage form is available either in single-dose pen or single-dose vial or multiple-dose KwikPen for four weeks. So, a patient needs to use/buy disposable pen every week or need to buy different pen injector for different doses as per approved dosage regimen and for the entire time period of the therapy. The pen provided for injecting is a single use pen, and should be thrown out after each dose is administered. This not only increases the cost of therapy to the patient but also unnecessary waste is generated which has an impact on the environment also. Further for better patient compliance and adherence to long term treatment.

Thus, it is required to a novel composition of tirzepatide that is more cost effective for patients, is stable enough to avoid use of single use pens for delivery, give better patient compliance and is environment friendly. With such a stable composition, it is possible to deliver multiple doses of tirzepatide using a multi-dose pen containing a one or more cartridge and the pen can be reused by replacing with a new cartridge or used for long term.

There still exists a need for a multi-dose pen of stable high concentration liquid composition of tirzepatide or pharmaceutically acceptable salts, or derivative thereof which is substantially free from sodium chloride, based on disclosure in U.S. Pat. No. 11,357,820 that such compositions lack enhanced stability as compared with compositions that include sodium chloride.

Accordingly, inventors of the present invention invented a stable sodium chloride free composition of high concentration tirzepatide or pharmaceutically acceptable salts, or derivative(s) thereof with concentration of 67 mg/mL to 200 mg/mL used for the treatment of tirzepatide sensitive diseases, which composition surprisingly exhibiting stability suitable for long-term storage.

OBJECT OF THE INVENTION

An object of the present invention relates to a multi-dose pen comprising a liquid pharmaceutical composition of tirzepatide or pharmaceutically acceptable salt or derivative(s) thereof.

Another object of the present invention relates to a multi-dose pen comprising a liquid pharmaceutical composition of tirzepatide or pharmaceutically acceptable salt or derivative(s) thereof at a concentration of 67 mg/mL to 200 mg/mL.

Another object of the present invention relates to a multi-dose pen comprising a liquid pharmaceutical composition of tirzepatide in a concentration of 67 mg/mL to 200 mg/mL, wherein the composition is substantially free from sodium chloride, and wherein such composition exhibits long-term stability suitable for storage.

Another object of the present invention relates to a multi-dose pen that is reusable or disposable.

Another object of the present invention relates to a multi-dose pen comprising more than one dosage of 10 mg or 12.5 mg or 15 mg.

Another object of the present invention relates to a multi-dose single pen comprising twelve doses of any one of 10 mg, 12.5 mg or 15 mg.

It is yet another object of the present invention to provide a multi-dose pen comprising a composition of tirzepatide or pharmaceutically acceptable salt or derivative(s) thereof for use in the treatment of tirzepatide sensitive diseases.

SUMMARY OF THE INVENTION

The present invention relates to a multi-dose pen comprising a liquid pharmaceutical composition of tirzepatide or pharmaceutically acceptable salt or derivative(s) thereof.

The present invention relates to a multi-dose pen comprising a liquid pharmaceutical composition of tirzepatide or pharmaceutically acceptable salt or derivative(s) thereof at a concentration of 67 mg/mL to 200 mg/mL.

The present invention relates to a multi-dose pen comprises liquid pharmaceutical composition of tirzepatide or pharmaceutically acceptable salt or derivative(s) thereof at a concentration of 67 mg/mL to 200 mg/mL, wherein the composition is substantially free from sodium chloride, and wherein such composition exhibits long-term stability suitable for storage.

The present invention relates to a multi-dose pen comprising a liquid pharmaceutical composition of tirzepatide or pharmaceutically acceptable salt or derivative(s) thereof at a concentration of 67 mg/mL to 200 mg/mL, wherein the composition is substantially free from sodium chloride; wherein the multi-dose pen is reusable or disposable.

The present invention relates to a multi-dose pen comprising more than one dosage of tirzepatide as 10 mg or 12.5 mg or 15 mg for administration over a period of more than 1 week.

The present invention relates to a multi-dose single pen comprising twelve doses of any one of 10 mg, 12.5 mg or 15 mg.

The present invention further relates to a multi-dose pen as described herein, wherein the composition comprised in the multi-dose pen has less than 2.5% total impurities after storage for 6 months at 2-8° C.

The present invention relates to a multi-dose pen comprising a composition of tirzepatide or pharmaceutically acceptable salt or derivative(s) thereof for use in the treatment of tirzepatide sensitive diseases.

DETAILED DESCRIPTION

The present invention relates to a multi-dose pen comprises liquid pharmaceutical composition of tirzepatide or pharmaceutically acceptable salt or derivative(s) thereof at a concentration of 67 mg/mL to 200 mg/mL, wherein the composition is substantially free from sodium chloride; wherein the multi-dose pen is reusable or disposable.

Before the present process and methods are described, it is to be understood that this invention is not limited to particular compound(s), composition(s), embodiment(s), process described, that as such may, of course, vary.

Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms “a”, “and”, and “the” include plural referents unless the context clearly dictates otherwise.

As used herein, the words or terms set forth below have the following definitions:

The “active pharmaceutical ingredient” is tirzepatide or pharmaceutically acceptable salts, or derivative(s) thereof.

In one embodiment the term “treatment” or “treating” as used herein means the management and care of a patient for the purpose of combating a condition, such as a disease or a disorder. In one embodiment the term “treatment of tirzepatide sensitive diseases or disorders” is intended to include the full spectrum of treatments for a given condition from which the patient is suffering, such as administration of the active compound tirzepatide to alleviate the symptoms or complications; to delay the progression of the disease, disorder, or condition; to alleviate or relieve the symptoms and complications; and/or, to cure or eliminate the disease, disorder, or condition as well as to prevent the condition. In one embodiment prevention is to be understood as the management and care of a patient for the purpose of combating the disease, condition, or disorder and includes the administration of the active compound tirzepatide to prevent the onset of the symptoms or complications.

By “pharmaceutically acceptable excipient(s)”, it is meant any of the components of a pharmaceutical composition other than the active ingredients and which are approved by regulatory authorities or are generally regarded as safe for human or animal use.

The term “pharmaceutically acceptable salts” or “salts thereof” refers to derivative(s) of the disclosed compounds wherein the parent compound is modified by making acid or base salts, solvate, hydrate, esters and the like thereof. Pharmaceutically-acceptable salt forms of compounds provided herein are synthesized from the parent compound which contains a basic or acidic moiety by conventional chemical methods.

The term “pharmaceutically acceptable form” refers to any pharmaceutically acceptable form, including, solvates, hydrates, isomorphs, isomers, polymorphs, co-crystals, pseudomorphs, neutral forms, acid addition salt forms, prodrugs and derivative(s) thereof.

Herein, the term “pharmaceutical composition” or “composition” refers to a composition of a pharmaceutical active which renders the biological activity of the active ingredient therapeutically effective, but which does not include other ingredients which are obviously toxic to a subject to which the composition is intended to be administered. Further composition according to the invention comprise but are not limited to solid, semisolid, liquid dosage forms.

Non limiting examples of the composition of the invention include compositions in the form of liquids, ointments, gels, creams, and foams. Preferably composition in the form of solution. The term “solution” or “drug solution” or “medicament” is used herein as a synonym describing a pharmaceutical composition containing one or more active pharmaceutical ingredient(s) or a pharmaceutically acceptable salt or solvate thereof and optionally a pharmaceutically acceptable carrier. The term “composition” also refers to a “pharmaceutical composition” or “liquid pharmaceutical composition” or “liquid composition”.

The term “composition” or “formulation” or “preparation” is intended to encompass a combination including active ingredients and pharmaceutically acceptable excipients, as well as any product which results, directly or indirectly, from combination, complexation, or aggregation of any two or more of the ingredients, or from dissociation of one or more of the ingredients, or from other types of reactions or interactions involving one or more of the ingredients. The term “composition” or “dosage form” or “formulation” refers to finished pharmaceutical products that are suitable for administration, including, but not limited to, injections, etc.

The term “amount” as used herein refers to quantity or to concentration as appropriate to the context.

The “injectable composition” described herein include one or more active pharmaceutical ingredients. Any suitable active pharmaceutical ingredient can be employed, in any suitable amount, provided it effectively treats the disease or disorder in the subject. The amount of active pharmaceutical ingredient employed will typically depend on the active pharmaceutical ingredient as well as the disease or disorder to be treated.

The “stable pharmaceutical composition” described herein include one or more active pharmaceutical ingredients with pharmaceutical acceptable excipient(s) having physical and chemical stability.

The “stable pharmaceutical composition of tirzepatide or pharmaceutically acceptable salt or derivative thereof”

described herein comprises one or more pharmaceutical acceptable excipient(s) having physical and chemical stability.

The term "composition is substantially free from sodium chloride" or "substantially free from sodium chloride" refers to a composition free of sodium chloride. The term "substantially free", when used in relation to a given component of a composition (e.g., "composition substantially free from sodium chloride"), refers to a composition to which essentially none of said component has been added.

The composition according to the present invention can be substantially free of sodium chloride.

The term "composition administered by self-administer injection device" refers to a composition administered by a patient themselves by injection device.

In one embodiment, the present invention composition disclosed herein can be dispensed by a suitable device such as autoinjector devices, prefilled syringes, injection pen, ampoules, vials, a glass vial, a plastic vial and the like.

In another embodiment of the present invention, the composition may be administered by a self-administration injection device disclosed herein, which can be an autoinjector, injection pen, prefilled syringe, pre-filled syringe fully assembled into an auto-injector device and the like.

The term "composition administration by reusable or disposable injection device" refers to a herein can be a composition administered by a suitable device, either reusable or disposable.

The term "reusable" means pen can be used more than once for a specified single patient only with a replaceable primary container closure or drug container.

The term "disposable" means the pen can be used more than once for a single patient only with the same primary container closure or drug container in place and is discarded after the drug container is empty.

In another embodiment of the present invention, the composition that may be administered by self-administration injection device is a single-patient-use injection pen or pre-filled pen optionally with integrated needle.

The term "parenteral" as used herein, refers to the composition being administered by injection, infusion, or implantation into the human body. They may be directly administered or diluted before administration. The term "parenteral administration" as used herein is intramuscular, intraperitoneal, intra-abdominal, subcutaneous, intravenous, intraarterial, intradermal, intravitreal, intracerebral, intrathecal, epidural administration. In some embodiments, administration is subcutaneous.

The term "carrier" or "vehicle" or "solvent" or "diluent" or "excipient" or "excipient(s)" as used herein refers to pharmacologically inert materials that provide a more or less fluid matrix, suitable for parenteral drug administration. Carriers, vehicles or diluent useful herein include any such materials known in the art, which are nontoxic and do not interact with other components of a pharmaceutical composition or drug delivery system in a deleterious manner.

The term "about" or "approximately" means within 10% of a given value or range or within an acceptable error range for the particular value as determined by one of ordinary skill in the art, which will depend in part on how the value is measured or determined, i.e., the limitations of the measurement system. Alternatively, the term "about" means within an acceptable standard error of the mean.

The term "comprising" or "comprises" or "including" or "having" or "containing" is inclusive or open-ended i.e., comprising what is specified in the present invention, but not excluding other or additional aspects, unrecited elements or method steps.

When the term "further" or "additionally" is used herein, the unrecited elements, components may present along with the claimed cited element or components. It is to be construed as an open-ended term unless otherwise noted.

The term "optional" or "optionally" means that the subsequently described element, component or circumstance may or may not be present, so that the description includes instances where the element, component, or circumstance is included and instances where it is not.

The term "stability" or "stable" as used herein includes both physical and chemical stability. Stability parameters include but not limited to potency, stable pH value and other physico-chemical parameters. Peptide compositions are widely used as medicine. Most of the peptide drugs are formulated as liquid injectable compositions. The pharmaceutical composition of such peptides is required to be stable or to have a shelf life of several years in order to be suitable for use as medicine. However, peptide compositions are inherently unstable due to sensitivity towards physical and chemical degradation. To ensure the product's safety and efficacy, the peptide composition must meet defined quality and stability during and/or immediately after manufacture as well at the end of their designated shelf lives or during storage.

The term "stabilizer" refers to substances added to a product to maintain its physical and chemical properties over time. Stabilizers are used to improve the stability and efficacy of drugs. Stabilizers can help protect a drug from degradation, improve its solubility, bioavailability, and control its release time.

The term "preservative" refers to an agent added to a product as described to prevent (for some period of time) the growth of microorganisms, or the occurrence of undesirable chemical reactions (such as oxidation), that spoil or deteriorate, including deterioration of one or more utility, of the product.

The term "isotonicity agent" refers to a compound that is physiologically tolerated and imparts a suitable tonicity to a composition (e.g., immunogenic composition of the invention) to prevent the net flow of water across cell membranes that are in contact with the composition.

The term "potency" as used herein refers to the ability of a therapeutic agent to produce a desired effect after administration. The specific potency of a pharmacologically active ingredient refers to the concentration of the active ingredient that is required to achieve a given effect. It is usually expressed by the EC50-value which is the concentration of active ingredient that produces 50% of the maximum possible response to the active ingredient. Thus, the most potent active ingredient is the one with the lowest EC50-value. The specific efficacy of a pharmacologically active ingredient refers to the maximum level of response, which can be elicited by the active ingredient regardless of the dose for example, when an active ingredient has a high specific potency and a high specific efficacy, only a low concentration is necessary to achieve a high level of response. When an active ingredient has a low specific potency and a high specific efficacy, a high concentration is necessary to achieve a high level of response.

In one embodiment of present invention the composition pH is from about 6 to about 8. In another embodiment of present invention, the composition pH is from about 6.5 to about 7.5. In one embodiment of present invention a suitable pH adjuster may have been added to adjust the pH.

In another embodiment, the pharmaceutical composition of the present invention further comprises one or more pharmaceutically acceptable excipients such isotonicity agent, buffer, stabilizer, preservative and vehicle or solvent or carrier, and the like or mixtures thereof. The choice of excipients depends on the desired characteristics of the composition and on the nature of other pharmacologically active compounds in the composition. Suitable excipients are known to those skilled in the art (refer *Handbook of Pharmaceutical Excipients*, edited by Rowe et al, 6*th edition,* 2009).

Examples of stabilizers include but are not limited to dicarboxylic acids, polyols, amino acids, surfactants, poloxamer and its co-polymers. Suitable examples of stabilizers include polyethylene glycol or its derivative(s), polyvinyl alcohol, polyvinylpyrrolidone, carboxymethyl cellulose, L-glycine, L-histidine, imidazole, arginine, lysine, isoleucine, aspartic acid, tryptophan, threonine, or mixtures thereof.

Examples of isotonicity agents known generally in the art include but are not limited to disaccharide, mannitol, glycerol, sucrose, maltose, dextrose, trehalose, glycerin, propylene glycol, potassium chloride or pharmaceutically acceptable form and the like or mixtures thereof. Tonicity adjusting agents decrease the haemolysis of blood cells and reduce pain and irritation at the injection site.

In one embodiment, the composition of the invention comprises a buffer, such as phosphate, TRIS, citrate buffer and the like. In another embodiment, the phosphate buffer is a sodium phosphate buffer, such as disodium hydrogen phosphate dihydrate, sodium phosphate dibasic heptahydrate and the like.

Examples of preservatives include but not limited to benzyl alcohol, m-cresol, phenol, methyl parabens, propylparaben, butylparaben, chlorobutanol, thiomersal, phenylmercuric salts, or mixtures thereof. The sterile solution of the present invention comprises a preservative in amounts sufficient to maintain sterility of the solution in the injection device, throughout the shelf life of the product, which may be exposed to repeated multiple injections. This is because it is possible that the antimicrobial preservative concentration in a given preparation may decrease during the product's shelf life. In one embodiment, the optional preservative is phenol.

Examples of vehicles or carriers include but are not limited to water for injection, sterile water for injection, or hydroalcoholic solvents.

In one embodiment, the present invention composition can be administered to patients in need of treatment therewith by any appropriate route. Preferably the composition can be administered by different parenteral routes such as but not limited to, intradermal, subcutaneous, intramuscular, intravenous, intraperitoneal, intrathecal, epidural, intracardiac, intraarticular, intracavernous, intravitreal and the like.

In another embodiment of present invention provides stable injectable a composition can be administered by subcutaneous injection.

In one embodiment, the present invention composition may be in the form of injectable dosage forms, including but not limited to, suspension, solution, emulsion, nanosuspension, nanoemulsion, concentrated solutions for injections, ready to use or premix, ready to be dissolved in and/or diluted with a pharmaceutically acceptable vehicle, dry products ready to be dissolved in and/or diluted with a pharmaceutically acceptable vehicle, injectable microspheres, injectable microparticles, lyophilized powder for injection, spray dried powder for injection and the like.

In one embodiment, the present invention composition may be in the form of aqueous and/or non-aqueous injectable dosage forms.

In another embodiment of present invention composition comprises a liquid solution for administration to a subject.

In one embodiment, the present invention composition is prepared by the methods known in the art that maintain sterility, avoid the introduction of contaminants and microbial growth.

In one embodiment, the present invention is a multi-dose pen of tirzepatide or pharmaceutically acceptable salt or derivative(s) thereof.

In another embodiment, the present invention is a multidose pen of composition comprising tirzepatide or a pharmaceutically acceptable salt or derivative(s) thereof with one or more pharmaceutically acceptable excipient(s).

In another embodiment, the present invention is a multidose pen, comprising: a composition of tirzepatide; propylene glycol; buffer; and one or more pharmaceutically acceptable excipient(s); wherein the composition is substantially free from sodium chloride.

In another embodiment, the present invention is a multidose pen, comprising: a composition of tirzepatide; propylene glycol; phosphate buffer; phenol; and one or more pharmaceutically acceptable excipient(s); wherein the composition is substantially free from sodium chloride.

In another embodiment, the present invention is a multidose pen comprising: a composition of a) tirzepatide or pharmaceutically acceptable salts, or derivative(s) thereof at a concentration of 67 mg/ml to 200 mg/ml;
b) a tonicity adjuster;
c) a buffer;
d) optionally, a stabilizer;
a) optionally, a preservative; and
b) one or more pharmaceutically acceptable excipient(s);

wherein the composition is substantially free from sodium chloride, and wherein such composition exhibits long-term stability suitable for storage.

In another embodiment, the present invention is a multidose pen, comprising: a composition of a) tirzepatide 67 mg/mL to 200 mg/mL;
b) propylene glycol 1.4% w/v or less;
c) phosphate buffer 1.4% w/v or less;
d) phenol 0.55% w/v or less; and
e) one or more pharmaceutically acceptable excipient(s);

wherein composition is substantially free from sodium chloride.

In one embodiment, the present invention is a multi-dose pen, comprising: a composition of tirzepatide, or a pharmaceutically acceptable salt: wherein the tirzepatide concentration is 67 mg/mL to 200 mg/mL.

In another embodiment of present invention, the tirzepatide has a concentration of 67 mg/mL or more.

In one of embodiment, the tirzepatide concentration is from 67 mg/mL to 200 mg/mL. In another embodiments, the tirzepatide concentration is from 67 mg/mL to 150 mg/mL. In another embodiment the tirzepatide concentration is selected from the group comprising of 70 mg/mL, about 100 mg/mL, about 130 mg/mL, about 150 mg/mL, about 180 mg/mL, about 200 mg/mL and the like.

In another embodiment of present invention, the tirzepatide has a concentration of from 67 mg/mL to about 200 mg/mL, between the range of about 75 mg/mL to about 100 mg/mL, about 100 mg/mL to about 125 mg/mL, about 125 mg/mL to about 150 mg/mL, about 150 mg/mL to about 175 mg/mL. about 175 mg/mL to about 200 mg/mL and the like.

In another embodiment of present invention, the tirzepatide has a concentration of from 67 mg/mL to 80 mg/mL, about 80 mg/mL to about 100 mg/mL, about 100 mg/mL to about 120 mg/mL, about 120 mg/mL to about 140 mg/mL, about 140 mg/mL to about 160 mg/mL, about 160 mg/mL to about 180 mg/mL, about 180 mg/mL to about 200 mg/mL and the like.

In another embodiment of present invention, the tirzepatide has a concentration of from 67 mg/mL to 110 mg/mL, about 110 mg/mL to about 150 mg/mL, about 150 mg/mL to about 190 mg/mL, and the like.

In another embodiment of present invention, the tirzepatide has a concentration of from 67 mg/mL to 80 mg/mL, about 80 mg/mL to about 90 mg/mL, about 90 mg/mL to about 100 mg/mL, about 100 mg/mL to about 110 mg/mL, about 110 mg/mL to about 120 mg/mL, about 120 mg/mL to about 130 mg/mL, about 130 mg/mL to about 140 mg/mL, about 140 mg/mL to about 150 mg/mL, about 150 mg/mL to about 160 mg/mL, about 160 mg/mL to about 170 mg/mL, about 170 mg/mL to about 180 mg/mL, about 180 mg/mL to about 190 mg/mL, about 190 mg/mL to about 200 mg/mL, and the like.

In another embodiment of present invention, the tirzepatide has a concentration of from about 70 mg/mL to about 75 mg/mL, about 75 mg/mL to about 80 mg/mL, about 80 mg/mL to about 85 mg/mL, about 85 mg/mL to about 90 mg/mL, about 90 mg/mL to about 95 mg/mL, about 95 mg/mL to about 100 mg/mL, about 100 mg/mL to about 105 mg/mL, about 105 mg/mL to about 110 mg/mL, about 110 mg/mL to about 115 mg/mL, about 115 mg/mL to about 120 mg/mL, about 120 mg/mL to about 125 mg/mL, about 125 mg/mL to about 130 mg/mL, about 130 mg/mL to about 135 mg/mL, about 135 mg/mL to about 140 mg/mL, about 140 mg/mL to about 145 mg/mL, about 145 mg/mL to about 150 mg/mL, about 150 mg/mL to about 155 mg/mL, about 155 mg/mL to about 160 mg/mL, about 160 mg/mL to about 165 mg/mL, about 165 mg/mL to about 170 mg/mL, about 170 mg/mL to about 175 mg/mL, about 175 mg/mL to about 180 mg/mL, about 185 mg/mL to about 190 mg/mL, about 190 mg/mL to about 195 mg/mL, about 195 mg/mL to about 200 mg/mL and the like.

In one of embodiment, the composition volume is about 1000 μL or less. In one embodiment, the composition volume is about 900 μL or less. In one embodiment, the composition volume is about 800 μL or less. In one embodiment, the composition volume is about 700 μL or less. In one embodiment, the composition volume is about 600 μL or less. In one embodiment, the composition volume is about 500 μL or less. In one embodiment, the composition volume is about 400 μL or less. In one embodiment, the composition volume is about 300 μL or less. In one embodiment, the composition volume is about 200 μL or less. In one embodiment, the composition volume is about 100 μL or less.

In one embodiment, the composition volume is about 1000 μL or less. In one embodiment, the composition volume is about 900 μL or less. In one embodiment, the composition volume is about 800 μL or less.

In one embodiment, the composition volume is about 3000 μL or less. In one embodiment, the composition volume is about 2500 μL or less. In one embodiment, the composition volume is about 2000 μL or less. In one embodiment, the composition volume is about 1800 μL or less. In one embodiment, the composition volume is about 1500 μL or less. In one embodiment, the composition volume is about 1000 μL or less. In one embodiment, the composition volume is about 800 μL or less.

In embodiments, the composition comprised in the multi-dose pen exhibits long-term stability suitable for storage. In one embodiment, the composition has less than 2.5% total impurities after storage for 6 months at 2-8° C. In one embodiment, the composition has less than 2.0% total impurities after storage for 6 months at 2-8° C. In one embodiment, the composition has less than 1.0% total impurities after storage for 6 months at 2-8° C.

In one of the embodiments, the design of pen for delivery of doses from a reservoir is as shown below in Table 1.

TABLE 1

| Per mL | Conc. (Mg/ml) | Per Dose (Mg) | mL delivered per dose | Total Doses counts | Fill Volume (ml) |
|---|---|---|---|---|---|
| 1 | 67-200 | 10 | 0.05-0.15 | 20-60 | 3.0 |
| 1 | 67-200 | 12.5 | 0.06-0.18 | 16-48 | 3.0 |
| 1 | 67-200 | 15 | 0.07-0.22 | 13-40 | 3.0 |

In another embodiment, the design of pen for delivery of doses from a reservoir is as shown below in Table 2.

TABLE 2

| Per mL | Conc. (Mg/ml) | Dose (Mg) | mL delivered per dose | Total Dose counts | Fill Volume (ml) |
|---|---|---|---|---|---|
| 1 | 67-200 | 10 | 0.05-0.15 | 10-30 | 1.5 |
| 1 | 67-200 | 12.5 | 0.06-0.18 | 8-24 | 1.5 |
| 1 | 67-200 | 15 | 0.07-0.22 | 6-20 | 1.5 |

In another embodiment, the design of pen for delivery of doses from a reservoir is as shown below in Table 3.

TABLE 3

| Per mL | Conc. (Mg/ml) | Dose (Mg) | mL delivered per dose | Total Dose counts | Fill Volume (ml) |
|---|---|---|---|---|---|
| 1 | 67-200 | 10 | 0.05-0.15 | 5-16 | 0.8 |
| 1 | 67-200 | 12.5 | 0.06-0.18 | 4-12 | 0.8 |
| 1 | 67-200 | 15 | 0.07-0.22 | 3-10 | 0.8 |

In another embodiment, the design of pen for delivery of doses from a reservoir is as shown below in Table 4.

TABLE 4

| Per mL | Conc. (Mg/ml) | Dose (Mg) | mL delivered per dose | Total Dose counts | Fill Volume (ml) |
|---|---|---|---|---|---|
| 1 | 67-200 | 10 | 0.05-0.15 | 5-60 | 0.8-3 |
| 1 | 67-200 | 12.5 | 0.06-0.18 | 4-48 | 0.8-3 |
| 1 | 67-200 | 15 | 0.07-0.22 | 3-40 | 0.8-3 |

In another embodiment, the design of pen for delivery of doses from a reservoir is as shown below in Table 5.

TABLE 5

| Per mL | Conc. (Mg/ml) | Dose (Mg) | mL delivered per dose | Total Dose counts | Fill Volume (ml) |
|---|---|---|---|---|---|
| 1 | 67-200 | 10 | 0.01-0.60 | 5-60 | 0.8-3 |
| 1 | 67-200 | 12.5 | 0.01-0.60 | 4-48 | 0.8-3 |
| 1 | 67-200 | 15 | 0.01-0.60 | 3-40 | 0.8-3 |

In another embodiment, the design of pen for delivery of doses from a reservoir is as shown below in Table 6.

TABLE 6

| Conc. (Mg/ml) | Dose (Mg) | mL delivered per dose | Total Dose counts |
|---|---|---|---|
| 67-200 | 10 | 0.01-0.60 | 5-60 |
| 67-200 | 12.5 | 0.01-0.60 | 4-48 |
| 67-200 | 15 | 0.01-0.60 | 3-40 |

In another embodiment, the design of pen for delivery of doses from a reservoir is as shown below in Table 7.

TABLE 7

| Conc. (Mg/ml) | Dose (Mg) | mL delivered per dose | Total Dose counts |
|---|---|---|---|
| 67-200 | 10 | 0.05-0.15 | 5-60 |
| 67-200 | 12.5 | 0.06-0.18 | 4-48 |
| 67-200 | 15 | 0.07-0.22 | 3-40 |

In one embodiment, the multi-dose pen is for administration one week. In another embodiment, the multi-dose pen is for invention is for administration two weeks. In another embodiment, the multi-dose pen is for invention is for administration three weeks. In another embodiment, the multi-dose pen is for invention is for administration four weeks. In another embodiment, the multi-dose pen is for invention is for administration five weeks. In another embodiment, the multi-dose pen is for invention is for administration six weeks. In another embodiment, the multi-dose pen is for invention is for administration seven weeks. In another embodiment, the multi-dose pen is for invention is for administration eight weeks. In another embodiment, the multi-dose pen is for invention is for administration nine weeks. In another embodiment, the multi-dose pen is for invention is for administration ten weeks. In another embodiment, the multi-dose pen is for invention is for administration eleven weeks. In another embodiment, the multi-dose pen is for invention is for administration twelve weeks. In another embodiment, the multi-dose pen is for invention is for administration thirteen weeks. In another embodiment, the multi-dose pen is for invention is for administration fourteen weeks. In another embodiment, the multi-dose pen is for invention is for administration fifteen weeks. In another embodiment, the multi-dose pen is for invention is for administration sixteen weeks. In another embodiment, the multi-dose pen is for invention is for administration seventeen weeks. In another embodiment, the multi-dose pen is for invention is for administration eighteen weeks. In another embodiment, the multi-dose pen is for invention is for administration nineteen weeks. In another embodiment, the multi-dose pen is for invention is for administration twenty weeks, and the like.

In one embodiment, the multi-dose pen is for administration more than four weeks. In one embodiment, the multi-dose pen is for administration more than one month. In one embodiment, the multi-dose pen is for administration one month and above. In one embodiment, the multi-dose pen is for administration more than one month and up to 3 months.

In one embodiment, the multi-dose pen is for administration one dose for once weekly. In one embodiment, the multi-dose pen is for administration two doses for two weeks. In one embodiment, the multi-dose pen is for administration three doses for three weeks. In one embodiment, the multi-dose pen is for administration four doses for four weeks. In one embodiment, the multi-dose pen is for administration five doses for five weeks. In one embodiment, the multi-dose pen is for administration six doses for six weeks. In one embodiment, the multi-dose pen is for administration seven doses for seven weeks. In one embodiment, the multi-dose pen is for administration eight doses for eight weeks. In one embodiment, the multi-dose pen is for administration nine doses for nine weeks. In one embodiment, the multi-dose pen is for administration ten doses for ten weeks. In one embodiment, the multi-dose pen is for administration eleven doses for eleven weeks. In one embodiment, the multi-dose pen is for administration twelve doses for twelve weeks, and the like.

In one embodiment, the multi-dose pen is for administration after stabilization of glycaemic control in patients with type 2 diabetes or chronic weight management with 10 mg of tirzepatide for at least 4 weeks, then present invention dose of 10 mg can be administered and continued for further treatment.

In one embodiment, the multi-dose pen is for administration after stabilization of glycaemic control in patients with type 2 diabetes or chronic weight management with 10 mg of tirzepatide from a device different than that disclosed herein for at least 4 weeks, then the present invention multi-dose pen can be administered at a dose of 10 mg and continued for further treatment.

In one embodiment, the multi-dose pen is for administration after stabilization of glycaemic control in patients with type 2 diabetes or chronic weight management with 12.5 mg of tirzepatide for at least 4 weeks, then present invention dose of 12.5 mg can be administered and continued for further treatment.

In one embodiment, the multi-dose pen is for administration after stabilization of glycaemic control in patients with type 2 diabetes or chronic weight management with 12.5 mg of tirzepatide from a device different than that disclosed herein for at least 4 weeks, then the present invention multi-dose pen can be administered at a dose of 12.5 mg and continued for further treatment.

In one embodiment, the multi-dose pen is for administration after stabilization of glycaemic control in patients with type 2 diabetes or chronic weight management with 15 mg of tirzepatide for at least 4 weeks, then present invention dose of 15 mg can be administered and continued for further treatment.

In one embodiment, the multi-dose pen is for administration after stabilization of glycaemic control in patients with type 2 diabetes or chronic weight management with 15 mg of tirzepatide from a device different than that disclosed herein for at least 4 weeks, then the present invention multi-dose pen can be administered at a dose of 15 mg and continued for further treatment.

In one embodiment, method of administration comprises more than one dose of 10 mg or 12.5 mg or 15 mg for the stabilization of glycaemic control in patients with type 2 diabetes or chronic weight management, wherein method of administration does not comprise escalation of dose 10 mg, 12.5 mg and 15 mg.

In one embodiment, provided is a method of administration comprising more than one dose of 10 mg for the stabilization of glycaemic control in patients with type 2 diabetes or chronic weight management, wherein the method of administration does not comprise escalation of dose 10 mg.

In one embodiment, provided is a method of administration comprising more than one dose of 12.5 mg for the stabilization of glycaemic control in patients with type 2 diabetes or chronic weight management, wherein the method of administration does not comprise escalation of dose 12.5 mg.

In one embodiment, provided is a method of administration comprising more than one dose of 15 mg for the stabilization of glycaemic control in patients with type 2 diabetes or chronic weight management, wherein the method of administration does not comprise escalation of dose 15 mg.

In one embodiment, tirzepatide multi-dose pen is recommended for the long-term maintenance treatment of tirzepatide sensitive diseases or disorders such as glycaemic control in patients with type 2 diabetes or chronic weight management according to the following methods:

a) Inject 10 mg subcutaneously once weekly to patients who are stabilized with 10 mg dose for at least 4 weeks
b) Inject 12.5 mg subcutaneously once weekly to patients who are stabilized with 12.5 mg dose for at least 4 weeks
c) Inject 15 mg subcutaneously once weekly to patients who are stabilized with 15 mg dose for at least 4 weeks In one embodiment, the tirzepatide multi-dose pen comprises more than one doses of 10 mg or 12.5 mg or 15 mg.

In one embodiment, tirzepatide multi-dose pen comprises any one of a) the pen comprises twelve doses of 10 mg;
b) the pen comprises twelve doses of 12.5 mg; or
c) the pen comprises twelve doses of 15 mg.

In one embodiment, tirzepatide single multi-dose pen is comprises twelve doses of 10 mg.

In another embodiment, tirzepatide single multi-dose pen is comprises twelve doses of 12.5 mg.

In another embodiment, tirzepatide single multi-dose pen is comprises twelve doses of 15 mg.

In another embodiment, tirzepatide multi-dose pen is available in pre-filled, disposable, single-patient-multi dose pen.

In another embodiment, tirzepatide multi-dose pen is store in a refrigerator at 2° to 8° C. (36° to 46° F.).

In another embodiment, if needed each single patient multi-dose pen can be stored unrefrigerated at temperature not to exceed 25° C. (77° F.) for up to 90 days.

In another embodiment, the multi-dose pen is for administration over a period of one month. In another embodiment, the multi-dose pen is for administration over a period of two months. In one embodiment, the multi-dose pen is for administration over a period of three months. In another embodiment, the multi-dose pen is for administration over a period of four months. In another embodiment, the multi-dose pen is for administration over a period of five months. In another embodiment, the multi-dose pen is for administration over a period of six months. In another embodiment, the multi-dose pen is for administration over a period of seven months. In another embodiment, the multi-dose pen is for administration over a period of eight months. In another embodiment, the multi-dose pen is for administration over a period of nine months. In another embodiment, the multi-dose pen is for administration over a period of ten months. In another embodiment, the multi-dose pen is for administration over a period of eleven months. In another embodiment, the multi-dose pen is for administration over a period of twelve months or longer.

In another embodiment of present invention relates to a reusable or disposable pen comprises one or more cartridge(s) suitable for delivering multiple doses of tirzepatide.

In another embodiment of present invention is a multi-dose pen of tirzepatide or pharmaceutically acceptable form composition sterilized by the methods known in the art and filled in suitable containers. In another embodiment containers sterilization is done by the methods known in the art.

In another embodiment of present invention is a multi-dose pen of tirzepatide or pharmaceutically acceptable form composition; wherein composition administered by self-administer injection device.

In another embodiment of present invention is a multi-dose pen of tirzepatide or pharmaceutically acceptable form composition used for the treatment of tirzepatide sensitive diseases.

The present invention is further illustrated by reference to the following experiments which is for illustrative purpose only and does not limit the scope of the invention in any way.

EXAMPLES

TABLE 8

| Sr. No | Ingredient | Batch Composition mg/mL | Tirzepatide 10 mg | Tirzepatide 12.5 mg | Tirzepatide 15 mg |
|---|---|---|---|---|---|
| 1. | Tirzepatide | 100 mg/mL | 10 mg/0.5 mL | 12.5 mg/0.5 mL | 15 mg/0.5 mL |
| 2. | Propylene Glycol | 14 | — | — | — |
| 3. | Sodium Chloride | — | 4.1 | 4.1 | 4.1 |
| 4. | Phosphate Buffer | 1.42 | 0.7 | 0.7 | 0.7 |
| 5. | Phenol | 5.50 | — | — | — |
| 6. | WFI | q.s. to 1 mL | q.s. to 0.5 mL | q.s. to 0.5 mL | q.s. to 0.5 mL |

q.s.—quantum sufficient

Manufacturing Process i. Water is collected into a vessel was purged with nitrogen to reduce the dissolved oxygen (Do) content.
ii. Transferred one part of intended batch size of nitrogen purged water in mixing vessel.
iii. Under constant stirring dispensed quantity of phosphate buffer was added and stirred for adequate time with adequate speed.
iv. Under constant stirring dispensed quantity of propylene glycol was added and stirred for adequate time with adequate speed.
v. Under constant stirring dispensed quantity of phenol was added and stirred for adequate time with adequate speed.
vi. The temperature of the above composition was brought down to 2-8° C.; nitrogen purging was continued throughout the process.
vii. Dispensed quantity of tirzepatide was added to the above placebo composition and stirred for adequate time.

17

18 viii. pH of above composition pH was adjusted using a pH adjuster.

ix. Final volume made up to 100% using water for injection.

x. Stirred for adequate time for complete solubility.

xi. The above composition was filtered using 0.22 µm PVDF filter.

Summarized Stability Results for the Tested Compositions

Batch Composition Vs Tirzepatide Reference Sample 10 mg/12.5 mg/15 mg:

TABLE 9

| | Batch Composition | | | Tirzepatide 15 mg | Batch Composition | | Tirzepatide 15 mg | Tirzepatide 10 mg * | Tirzepatide 12.5 mg ** | Tirzepatide 15 mg *** |
|---|---|---|---|---|---|---|---|---|---|---|
| Condition | Initial | 02 W 2-8° C. | 06 M 2-8° C. | 06 M 2-8° C. | 02 W 25° C./ 60RH | 06 M 25° C./ 60RH | 06 M 25° C./ 60RH | Initial | Initial | Initial |
| Concentration | 100 mg/ mL | 100 mg/ mL | 100 mg/ mL | 15 mg/ 0.5 ml | 100 mg/ mL | 100 mg/ mL | 15 mg/ 0.5 ml | 10 mg/ 0.5 ml | 12.5 mg/ 0.5 mL | 15 mg/ 0.5 ml |
| Test | | | | | | Result | | | | |
| Description | CCS | CCS | CCS | CCS | CCS | CCS | CCS | CCS | CCS | CCS |
| pH | 6.98 | 6.98 | NA | NA | 6.96 | NA | NA | NA | NA | 6.99 |
| Osmolality mOsm/kg | 280 | NA | NA | 317 | NA | NA | 319 | 304 | 312 | 321 |
| Total Aggregate Content | 0.05 | 0.04 | 0.05 | 0.21 | 0.05 | 0.21 | 0.47 | 0.13 | 0.14 | 0.17 |
| Assay | 93.0 | 93.8 | 93.01 | 105.8 | 91.1 | 91.5 | 100.0 | NA | NA | NA |
| Total Impurity | 0.17 | 0.21 | 0.73 | 1.86 | 0.50 | 3.70 | 4.98 | 1.11 | 1.34 | 1.28 |

CCS—Clear colorless solution
W—Weeks
M—Months
Reference Age of the Samples
* 10 mg-10 Months;
** 12.5 mg-11 Months;
*** 15 mg-18 Months The design of multi-dose pen for delivery of doses from a reservoir is as shown below in Table 10:

TABLE 10

| Per mL | Conc. (Mg/ml) | Dose (Mg) | mL delivered per dose | Total Doses counts | Fill Volume (ml) |
|---|---|---|---|---|---|
| 1 | 100 | 10 | 0.1000 | 12 | 1.2 |
| 1 | 100 | 12.5 | 0.1250 | 12 | 1.5 |
| 1 | 100 | 15 | 0.1500 | 12 | 1.8 |

Surprisingly, the present inventors found that the high concentration tirzepatide composition of the present invention, wherein such composition is substantially free from sodium chloride, maintained physical stability which was a surprising and unexpected development.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

We claim:

1. A multi-dose pen comprising:
a composition of tirzepatide or pharmaceutically acceptable salt or derivative(s) thereof at a concentration of 67 mg/ml to 200 mg/ml with one or more pharmaceutically acceptable excipient(s),
wherein the composition has less than 2.5% total impurities after storage for 6 months at 2-8° C.

2. The multi-dose pen according to claim 1, wherein the pen is reusable or disposable.

3. The multi-dose pen according to claim 1, wherein the pen comprises more than one doses of 10 mg, 12.5 mg or 15 mg.

4. The multi-dose pen according to claim 1, wherein any one of
a) the pen comprises twelve doses of 10 mg
b) the pen comprises twelve doses of 12.5 mg; or
c) the pen comprises twelve doses of 15 mg.

5. The multi-dose pen according to claim 1, wherein the composition is substantially free from sodium chloride.

6. The multi-dose pen according to claim 1, wherein the composition is administered for longer than a week.

7. The multi-dose pen according to claim 1, comprising:
a composition of
a) tirzepatide or pharmaceutically acceptable salts, or derivative(s) thereof at a concentration 67 mg/ml to 200 mg/ml;
b) a tonicity adjuster;
c) a buffer;
d) a stabilizer;
e) a preservative; and
f) one or more pharmaceutically acceptable excipient(s);
wherein the composition is substantially free from sodium chloride.

8. A method of administering the multi-dose pen according to claim 1, wherein the method of administration comprises more than one doses of 10 mg, or 12.5 mg or 15 mg for the stabilization of glycaemic control in patients with type 2 diabetes or chronic weight management, wherein the method of administration does not comprise escalation of dosages 10 mg, 12.5 mg and 15 mg.

9. A method of administering the multi-dose pen according to claim 1, wherein the method of administration comprises stabilization of glycaemic control in patients with type 2 diabetes or chronic weight management with 10 mg or 12.5 mg or 15 mg doses after 4 weeks of tirzepatide followed by administration of the multi-dose pen of 10 mg, 12.5 mg or 15 mg doses.

10. The multi-dose pen according to claim 1, wherein the composition is used for the treatment of tirzepatide sensitive diseases or disorders.

* * * * *